US012797030B2

(12) United States Patent
Kitano

(10) Patent No.: US 12,797,030 B2
(45) Date of Patent: Nov. 17, 2026

(54) RADIOGRAPHY SYSTEM, RADIOGRAPHY METHOD, AND RADIOGRAPHY PROGRAM

(71) Applicant: FUJIFILM CORPORATION, Tokyo (JP)

(72) Inventor: Koichi Kitano, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 127 days.

(21) Appl. No.: 18/967,478

(22) Filed: Dec. 3, 2024

(65) Prior Publication Data

US 2025/0204880 A1 Jun. 26, 2025

(30) Foreign Application Priority Data

Dec. 22, 2023 (JP) ................................ 2023-217394

(51) Int. Cl.
*A61B 6/00* (2024.01)
*G16H 30/40* (2018.01)

(52) U.S. Cl.
CPC ............. *A61B 6/545* (2013.01); *A61B 6/487* (2013.01); *A61B 6/547* (2013.01); *G16H 30/40* (2018.01)

(58) Field of Classification Search
CPC ......... A61B 6/545; A61B 6/487; A61B 6/547; A61B 6/06; A61B 6/4464; A61B 6/588; A61B 6/54; A61B 6/00; G16H 30/40
See application file for complete search history.

(56) References Cited

U.S. PATENT DOCUMENTS 6,222,906 B1 * 4/2001 Sakaguchi .............. A61B 6/06 378/95
2009/0032744 A1 2/2009 Kito et al.
2017/0143286 A1 * 5/2017 Exelmans ........... A61B 6/4233
2018/0368797 A1 12/2018 Kuwata et al.
2021/0077051 A1 3/2021 Kuwata et al.
2021/0383558 A1 12/2021 Miyazaki
2024/0138784 A1 * 5/2024 Litzenberger ........... A61B 6/12

FOREIGN PATENT DOCUMENTS

JP H09-114044 A 5/1997
JP 2006-255281 A 9/2006
JP 2019-005073 A 1/2019
WO 2021/216967 A1 10/2021

OTHER PUBLICATIONS

Extended European Search Report dated May 8, 2025, issued in corresponding EP Patent Application No. 24217518.0.

* cited by examiner

*Primary Examiner* — Courtney D Thomas
(74) *Attorney, Agent, or Firm* — SOLARIS Intellectual Property Group, PLLC

(57) ABSTRACT

Provided are a radiography system, a radiography method, and a radiography program that can improve an imaging efficiency in a radiography system capable of executing fluoroscopy and general imaging in a switchable manner. A radiography system sets an imaging mode to a fluoroscopy mode in a case where a condition that an irradiation area of radiation on a detection surface of a radiation detector is equal to or less than a maximum area capable of detecting the radiation in the radiation detector is satisfied, and causes the radiation detector to start processing of continuously acquiring an image at a predetermined frame rate regardless of whether or not an instruction to start irradiation with the radiation is received in a case where the imaging mode is the fluoroscopy mode.

19 Claims, 7 Drawing Sheets

RADIOGRAPHY SYSTEM, RADIOGRAPHY METHOD, AND RADIOGRAPHY PROGRAM

CROSS-REFERENCE TO RELATED APPLICATIONS

This application is based on and claims priority under 35 USC 119 from Japanese Patent Application No. 2023-217394, filed Dec. 22, 2023, the disclosure of which is incorporated herein by reference in its entirety.

BACKGROUND OF THE INVENTION

Technical Field

The present disclosure relates to a radiography system, a radiography method, and a computer-readable storage medium storing a radiography program.

Related Art

JP2006-255281A discloses a technique for measuring a distance between an X-ray source and an X-ray detection surface in an X-ray fluoroscopy apparatus.

In a medical field, for example, fluoroscopy is performed for the purpose of assisting in an examination such as a gastric barium examination and a cystography, or a treatment such as orthopedic reduction. In addition, even in a case where the purpose is to assist in the examination or the treatment, general imaging may be performed in addition to the fluoroscopy to leave one radiation image for recording. In this case, it is preferable that the fluoroscopy and the general imaging can be executed in a switchable manner by one system, because an imaging efficiency can be improved. In the technique disclosed in JP2006-255281A, it is not considered to perform the fluoroscopy and the general imaging in a switchable manner. The fluoroscopy means continuously capturing a plurality of radiation images at a predetermined frame rate (that is, moving image capturing). In addition, the general imaging means recording one radiation image according to an imaging instruction from a user such as a radiologist (that is, still image capturing).

SUMMARY

The present disclosure has been made in view of the above circumstances, and an object of the present disclosure is to provide a radiography system, a radiography method, and a computer-readable storage medium storing a radiography program that can improve an imaging efficiency in a radiography system capable of executing fluoroscopy and general imaging in a switchable manner.

According to a first aspect of the present invention, there is provided a radiography system capable of executing fluoroscopy in which a plurality of radiation images are continuously captured at a predetermined frame rate and general imaging in which one radiation image is recorded in a switchable manner, the radiography system comprising at least one processor, in which the processor is configured to: set an imaging mode to a fluoroscopy mode in a case where a condition that an irradiation area of radiation on a detection surface of a radiation detector is equal to or less than a maximum area capable of detecting the radiation in the radiation detector is satisfied; and cause the radiation detector to start processing of continuously acquiring an image at the predetermined frame rate regardless of whether or not an instruction to start irradiation with the radiation is received in a case where the imaging mode is the fluoroscopy mode.

According to a second aspect, in the radiography system according to the first aspect, the processor is configured to, in a case where the condition that the irradiation area is equal to or less than the maximum area is satisfied, notify that the condition is satisfied.

According to a third aspect, in the radiography system according to the first or second aspect, the processor is configured to set the imaging mode to a general imaging mode in a case where the condition that the irradiation area is equal to or less than the maximum area is not satisfied.

According to a fourth aspect, in the radiography system according to any one of the first to third aspects, the condition is a condition that a distance from a radiation source to the detection surface is equal to or less than a set value.

According to a fifth aspect, in the radiography system according to any one of the first to fourth aspects, a plurality of processors are provided, and a first processor that performs image processing on the radiation image obtained in a case where the imaging mode is a general imaging mode and a second processor that performs image processing on the radiation image obtained in a case where the imaging mode is the fluoroscopy mode are different processors.

According to a sixth aspect, in the radiography system according to the fifth aspect, the second processor includes a logic circuit in which logic of image processing performed on the radiation image is programmed in advance.

According to a seventh aspect, in the radiography system according to any one of the first to sixth aspects, the processor is configured to, in a case where the imaging mode is the fluoroscopy mode, and an instruction to capture a still image is received, generate a single radiation still image using one or more radiation images obtained by the fluoroscopy.

According to an eighth aspect, in the radiography system according to the fourth aspect, the processor is configured to receive designation of the set value.

According to a ninth aspect, there is provided a radiography method for a radiography system including at least one processor and capable of executing fluoroscopy in which a plurality of radiation images are continuously captured at a predetermined frame rate and general imaging in which one radiation image is recorded in a switchable manner, the radiography method comprising: causing the processor to execute processing of setting an imaging mode to a fluoroscopy mode in a case where a condition that an irradiation area of radiation on a detection surface of a radiation detector is equal to or less than a maximum area capable of detecting the radiation in the radiation detector is satisfied, and causing the radiation detector to start processing of continuously acquiring an image at the predetermined frame rate regardless of whether or not an instruction to start irradiation with the radiation is received in a case where the imaging mode is the fluoroscopy mode.

According to a tenth aspect, there is provided a computer-readable storage medium storing a radiography program for a radiography system including at least one processor and capable of executing fluoroscopy in which a plurality of radiation images are continuously captured at a predetermined frame rate and general imaging in which one radiation image is recorded in a switchable manner, the radiography program causing the processor to execute processing of: setting an imaging mode to a fluoroscopy mode in a case where a condition that an irradiation area of radiation on a detection surface of a radiation detector is equal to or less than a maximum area capable of detecting the radiation in the radiation detector is satisfied; and causing the radiation detector to start processing of continuously acquiring an image at the predetermined frame rate regardless of whether or not an instruction to start irradiation with the radiation is received in a case where the imaging mode is the fluoroscopy mode.

According to the present disclosure, in a radiography system capable of executing fluoroscopy and general imaging in a switchable manner, it is possible to improve an imaging efficiency.

DETAILED DESCRIPTION

Hereinafter, exemplary embodiments for implementing the technique of the present disclosure will be described in detail with reference to the drawings.

Figure 1:
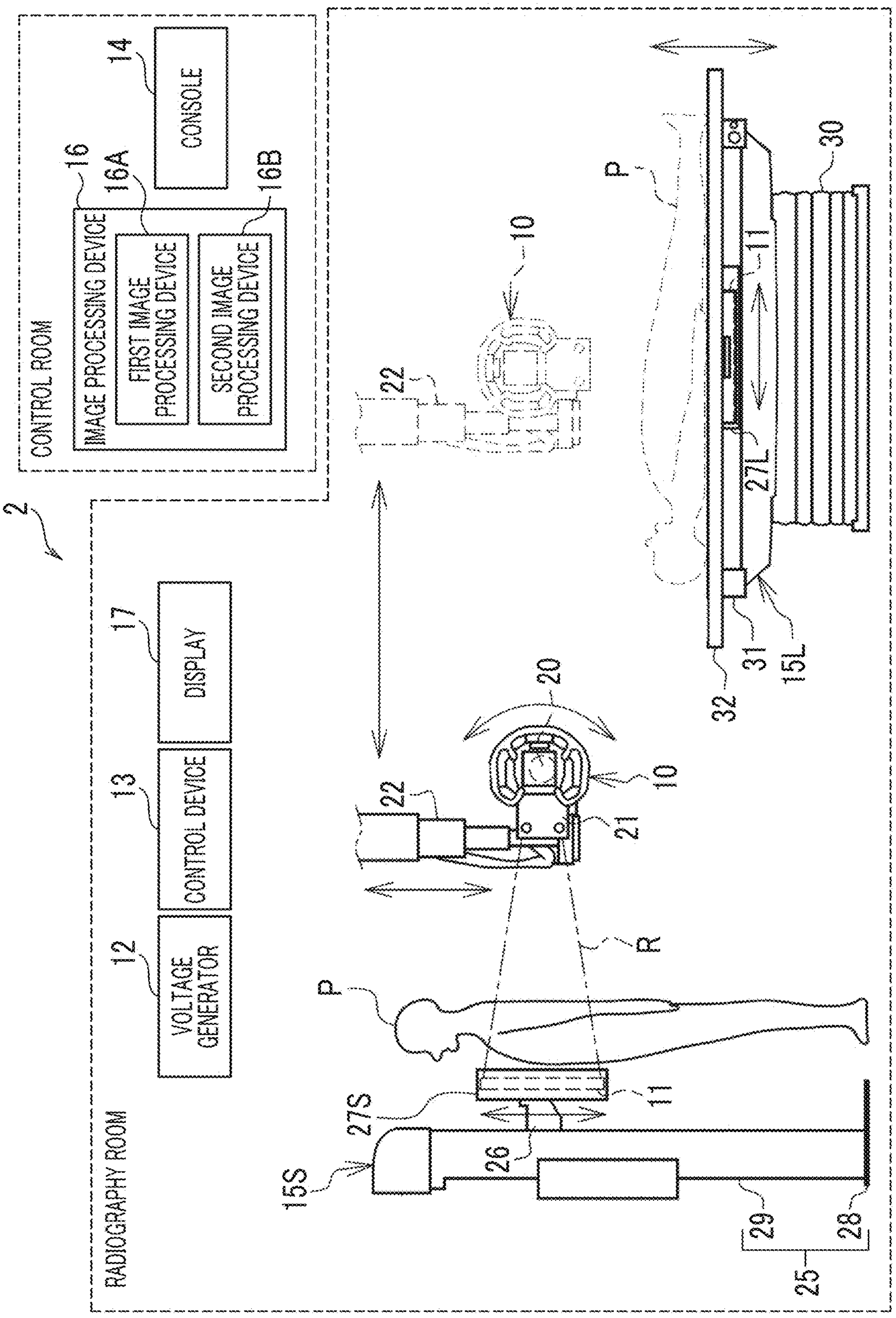
FIG. 1 is a diagram showing an example of a radiography system.

First, a configuration of a radiography system 2 will be described with reference to FIG. 1. As shown in FIG. 1, the radiography system 2 is a system that irradiates a patient Pas an example of a subject with radiation R, such as X-rays or y-rays, and captures a radiation image of the patient P, and is operated by an operator such as a radiologist. The radiography system 2 can switch and execute fluoroscopy that continuously captures a plurality of radiation images at a predetermined frame rate and general imaging that records one radiation image. The radiography system 2 includes a radiation source 10, a radiation detector 11, a voltage generator 12, a control device 13, a console 14, an upright imaging stand 15S, a decubitus imaging table 15L, an image processing device 16, and a display 17. The radiation source 10, the radiation detector 11, the voltage generator 12, the control device 13, the upright imaging stand 15S, the decubitus imaging table 15L, and the display 17 are installed in, for example, a radiography room of a medical facility. Meanwhile, the console 14 and the image processing device 16 are installed in, for example, a control room adjacent to the radiography room. One radiation source 10 and one radiation detector 11 are prepared, and are used in common in the upright imaging stand 15S and the decubitus imaging table 15L.

The radiation source 10 includes a radiation tube 20 that emits the radiation R and an irradiation field limiter (also referred to as a collimator) 21 that limits an irradiation field of the radiation R. The radiation tube 20 is provided with, for example, a filament, a target, a grid electrode, and the like. A voltage is applied between the filament as a cathode and the target as an anode from the voltage generator 12. The voltage that is applied between the filament and the target is referred to as a tube voltage. The filament releases thermoelectrons according to the applied tube voltage toward the target. The target radiates the radiation R with collision of the thermoelectrons released from the filament. The grid electrode is disposed between the filament and the target. The grid electrode changes a flow rate of the thermoelectrons from the filament toward the target according to the voltage applied from the voltage generator 12. The flow rate of the thermoelectrons from the filament toward the target is referred to as a tube current.

An incident opening through which the radiation R from the radiation tube 20 is incident and an exit opening through which the radiation R exits are formed in the irradiation field limiter 21. Four shielding plates are provided in the vicinity of the exit opening. The shielding plate is formed of a material that shields the radiation R, for example, lead. The shielding plates are each disposed on each side of a quadrangle, in other words, are assembled in a checkered pattern and form a quadrangular irradiation opening through which the radiation R is transmitted. The irradiation field limiter 21 changes a size of the irradiation opening by changing a position of each shielding plate, thereby changing an irradiation field of the radiation R.

The radiation source 10 is suspended from a ceiling of the radiography room by a support column 22. The support column 22 is attached to a rail turned around the ceiling through a wheel. The support column 22 and the radiation source 10 are movable in a horizontal direction in the radiography room by the rail and the wheel. The support column 22 is extendable in a height direction, and accordingly, the radiation source 10 is movable in the height direction. The radiation source 10 is rotatable with respect to the support column 22 with an axis perpendicular to a paper surface as a rotation axis.

In addition, the radiation source 10 includes a position sensor that detects a position of the radiation source 10. For example, the position sensor comprises a variable resistor and detects the position of the radiation source 10 based on a resistance value of the variable resistor that changes according to the position of the radiation source 10. The position of the radiation source 10 is represented by, for example, an orthogonal coordinate system composed of three axes of an X-axis, a Y-axis, and a Z-axis that are orthogonal to each other. The position of the radiation source 10 detected by the position sensor is transmitted to the control device 13.

The radiation detector 11 is portable, and detects the radiation R transmitted through the patient P to output the radiation image of the patient P. The radiation detector 11 transmits the radiation image to the image processing device 16. The radiation detector 11 is used while being accommodated in the upright imaging stand 15S or the decubitus imaging table 15L. In addition, the radiation detector 11 may be used in a state of being removed from the upright imaging stand 15S or the decubitus imaging table 15L in the radiography room and held by the patient P, or may be used in a state of being placed under the patient P who is lying on a bed in a hospital room. FIG. 1 illustrates an aspect in which the radiation image of the chest of the patient P positioned in front of the upright imaging stand 15S is captured.

The voltage generator 12 generates a tube voltage to be applied to the radiation tube 20. The voltage generator 12 and the radiation tube 20 are connected by a voltage cable. The tube voltage generated by the voltage generator 12 is supplied to the radiation tube 20 through the voltage cable.

The control device 13 controls an operation of the radiation source 10 via the voltage generator 12 according to an irradiation condition of the radiation R. The irradiation condition includes the tube voltage and the tube current applied to the radiation tube 20 and an irradiation time of the radiation R. Further, instead of the tube current and the irradiation time, a product of the tube current and the irradiation time, that is, a so-called mAs value may be used as the irradiation condition. In the fluoroscopy, the control device 13 decides the irradiation condition in the next frame based on a dose of the radiation R that has reached the radiation detector 11, which is derived from the radiation image of the previous frame. As a result, the control device 13 performs dose control of the radiation R in each frame during irradiation with the radiation R in the fluoroscopy.

A start instruction for the radiography is input by the operator to the control device 13 through an irradiation switch (not shown). The irradiation switch is installed in at least one of the control room or the radiography room. The irradiation switch may be a switch operated by a hand or a switch operated by a foot. In a case where the start instruction is input, the control device 13 operates the voltage generator 12 according to the irradiation condition to emit the radiation R from the radiation tube 20.

In addition, the control device 13 derives a distance (hereinafter, referred to as a "source to image receptor distance (SID)") from the radiation source 10 to a detection surface of the radiation detector 11 accommodated in an upright posture holder 27S or a decubitus posture holder 27L. As described above, the control device 13 acquires the position of the radiation source 10 transmitted from the position sensor. In addition, positions of the upright posture holder 27S and the decubitus posture holder 27L are known. Therefore, the control device 13 can derive the SID in a case where the radiation detector 11 is accommodated in the upright posture holder 27S, based on the position of the radiation source 10 and the position of the upright posture holder 27S. In addition, the control device 13 can derive the SID in a case where the radiation detector 11 is accommodated in the decubitus posture holder 27L, based on the position of the radiation source 10 and the position of the decubitus posture holder 27L. In the following, it is assumed that the SID is known by deriving the SID by the control device 13 each time the radiation source 10 is moved.

The console 14 is, for example, a personal computer. An imaging order 66, which will be described below, is registered in advance in the console 14.

The upright imaging stand 15S includes a stand 25, a connection portion 26, the upright posture holder 27S, and the like. The stand 25 is configured with a pedestal 28 that is installed on a floor surface of the radiography room, and a support column 29 that extends from the pedestal 28 in the height direction. The connection portion 26 connects the upright posture holder 27S to the stand 25. The connection portion 26 and the upright posture holder 27S are movable in the height direction with respect to the support column 29 and can perform height adjustment according to the height of the patient Por an imaging site.

The upright posture holder 27S has a box shape and accommodates the radiation detector 11 therein. The upright posture holder 27S is mostly formed of a conductive material having an electromagnetic wave shielding property, such as aluminum or stainless steel. The upright posture holder 27S has a front surface facing the radiation source 10, and the front surface is formed of a material transmitting the radiation R, such as carbon.

The decubitus imaging table 15L has a pedestal 30 that is installed on the floor surface of the radiography room, a connection portion 31, a top plate 32, the decubitus posture holder 27L, and the like. The connection portion 31 connects the top plate 32 to the pedestal 30. The pedestal 30 is of an elevating type, and thus heights of the top plate 32 and the decubitus posture holder 27L can be adjusted. The top plate 32 has a rectangular plate shape having a length and a width such that the patient P can lie, and is formed of a material transmitting the radiation R, such as carbon.

The decubitus posture holder 27L is disposed in a space between the pedestal 30 and the top plate 32 formed by the connection portion 31. The decubitus posture holder 27L has a box shape with a top covered with the top plate 32, and accommodates the radiation detector 11 therein. The decubitus posture holder 27L is formed of a conductive material having an electromagnetic wave shielding property, such as aluminum or stainless steel. The decubitus posture holder 27L is slidable in a direction along a longitudinal direction of the top plate 32 by a sliding mechanism.

The image processing device 16 includes a first image processing device 16A and a second image processing device 16B. The first image processing device 16A is a general-purpose computer such as a personal computer and performs image processing on a radiation image obtained by general imaging. The second image processing device 16B is a computer dedicated to fluoroscopy and performs image processing on a radiation image obtained by fluoroscopy.

The display 17 is a liquid crystal display or an electro luminescence (EL) display. The display 17 is installed on a display cart with a caster and is movable in the radiography room. The display 17 is connected to the image processing device 16.

Figure 2:
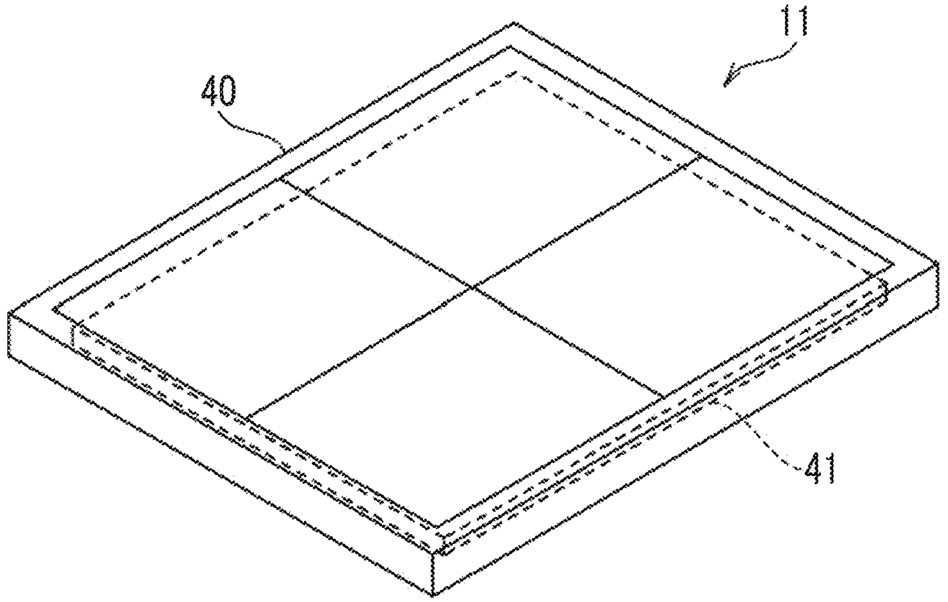
FIG. 2 is a diagram showing an example of a radiation detector.

As shown in FIG. 2, the radiation detector 11 has a housing 40 and a detection panel 41. The housing 40 has a flat, generally rectangular parallelepiped shape with a rectangular plane shape, and houses the detection panel 41 therein. Most of a front surface of the housing 40 is formed of a material transmitting the radiation R, such as carbon. The radiation detector 11 is set in the upright posture holder 27S or the decubitus posture holder 27L in a posture in which the front surface of the housing 40 faces the radiation source 10.

The detection panel 41 has a configuration in which a plurality of pixels that are sensitive to the radiation R or visible light converted from the radiation R by a scintillator to generate signal charges are arranged. In addition to the detection panel 41, a control device 18 described below is incorporated in the housing 40. In addition, a communication unit, a battery that supplies power to each unit, and the like are also incorporated in the housing 40. The radiation detector 11 may be a so-called computed radiography (CR) cassette in which an imaging plate is incorporated in place of the detection panel 41.

A surface of the housing 40 which is irradiated with the radiation R corresponds to the detection surface of the radiation detector 11. In the present embodiment, an area of the detection surface composed of all the pixels in the detection panel 41 is the maximum area capable of detecting the radiation R in the radiation detector 11.

Figure 3:
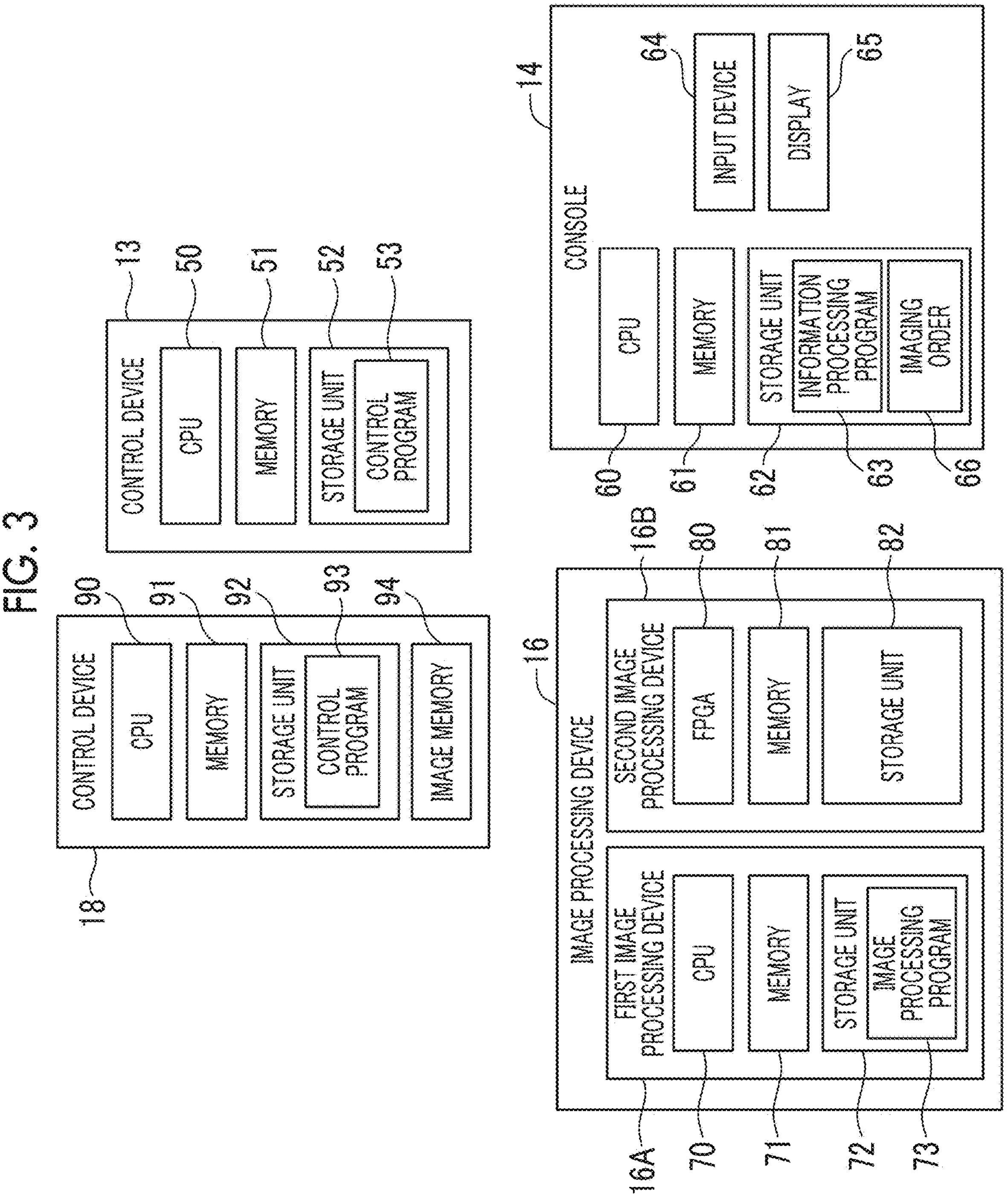
FIG. 3 is a block diagram showing an example of a hardware configuration of each device constituting the radiography system.

Next, hardware configurations of the control device 13, the console 14, the first image processing device 16A, the second image processing device 16B, and the control device 18 will be described with reference to FIG. 3. As shown in FIG. 3, the control device 13 includes a central processing unit (CPU) 50, a memory 51 as a temporary storage area, and a non-volatile storage unit 52. The CPU 50 is an example of a processor.

The storage unit 52 is realized by a hard disk drive (HDD), a solid state drive (SSD), a flash memory, or the like. The storage unit 52 as a storage medium stores a control program 53. The CPU 50 reads out the control program 53 from the storage unit 52, loads the control program 53 into the memory 51, and executes the loaded control program 53.

The console 14 includes a CPU 60, a memory 61 as a temporary storage area, a non-volatile storage unit 62, an input device 64 such as a keyboard and a mouse, and a display 65 such as a liquid crystal display or an EL display. The CPU 60 is an example of a processor.

The storage unit 62 is realized by an HDD, an SSD, a flash memory, or the like. An information processing program 63 is stored in the storage unit 62 as a storage medium. The CPU 60 reads out the information processing program 63 from the storage unit 62, loads the information processing program 63 into the memory 61, and executes the loaded information processing program 63.

In addition, the storage unit 62 stores the imaging order 66 that is registered in advance. The imaging order 66 includes an irradiation condition of the radiation R as an example of an imaging condition of the radiation image in the general imaging and an irradiation condition of the radiation R as an example of an imaging condition of the radiation image in the fluoroscopy. In addition, the imaging order 66 includes patient information such as an age of the patient P, information on a physique of the patient P, and the imaging site.

The first image processing device 16A includes a CPU 70, a memory 71 as a temporary storage area, and a non-volatile storage unit 72. The CPU 70 is an example of a processor. The storage unit 72 is realized by an HDD, an SSD, a flash memory, or the like. An image processing program 73 is stored in the storage unit 72 as a storage medium. The CPU 70 reads out the image processing program 73 from the storage unit 72, loads the image processing program 73 into the memory 71, and executes the loaded image processing program 73.

The second image processing device 16B includes a field programmable gate array (FPGA) 80, a memory 81 as a temporary storage area, and a non-volatile storage unit 82. The FPGA 80 is an example of a processor. The storage unit 82 is realized by an HDD, an SSD, a flash memory, or the like. The FPGA 80 includes a logic circuit in which logic of image processing performed on the radiation image is programmed in advance.

The control device 18 includes a CPU 90, a memory 91 as a temporary storage area, a non-volatile storage unit 92, and an image memory 94. The CPU 90 is an example of a processor. The storage unit 92 is realized by an HDD, an SSD, a flash memory, or the like. The storage unit 92 as a storage medium stores a control program 93. The CPU 90 reads out the control program 93 from the storage unit 92, loads the control program 93 into the memory 91, and executes the loaded control program 93. The image memory 94 has a storage capacity capable of storing a predetermined number of radiation images.

Figure 4:
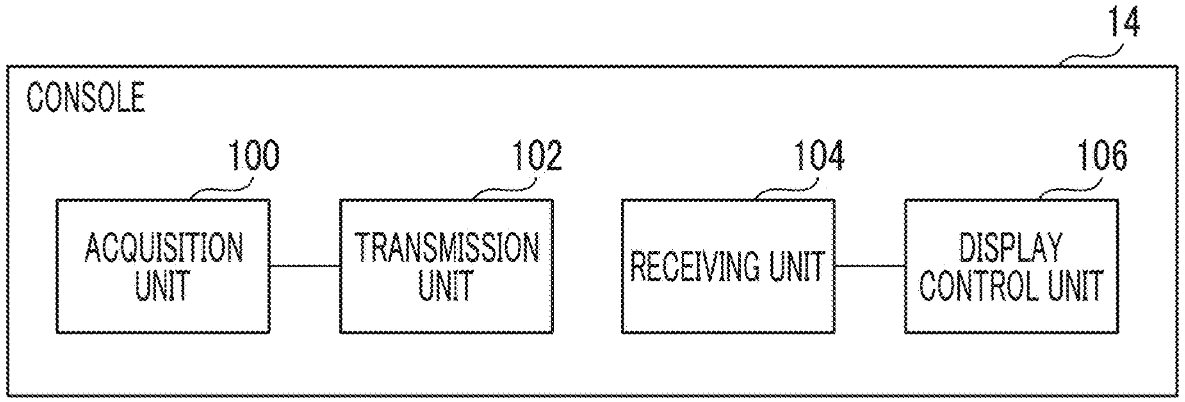
FIG. 4 is a block diagram showing an example of a functional configuration of a console.

Next, a functional configuration of the console 14 will be described with reference to FIG. 4. As shown in FIG. 4, the console 14 includes an acquisition unit 100, a transmission unit 102, a receiving unit 104, and a display control unit 106. The CPU 60 executes the information processing program 63 to function as the acquisition unit 100, the transmission unit 102, the receiving unit 104, and the display control unit 106.

The acquisition unit 100 acquires the imaging order 66 from the storage unit 62. The transmission unit 102 transmits the irradiation condition in the general imaging and the irradiation condition in the fluoroscopy imaging according to the imaging order 66 acquired by the acquisition unit 100, to the control device 13.

The receiving unit 104 receives the radiation image obtained by the general imaging transmitted from the first image processing device 16A. In addition, the receiving unit 104 receives the radiation image obtained by the fluoroscopy transmitted from the second image processing device 16B. In the following, in a case where the radiation image obtained by the general imaging and the radiation image obtained by the fluoroscopy are distinguished, the radiation image obtained by the general imaging is referred to as a "first radiation image", and the radiation image obtained by the fluoroscopy is referred to as a "second radiation image".

The display control unit 106 performs control to display the first radiation image received by the receiving unit 104 on the display 65. In addition, the display control unit 106 performs control to display a plurality of the second radiation images continuously received by the receiving unit 104 on the display 65 according to a frame rate.

Figure 5:
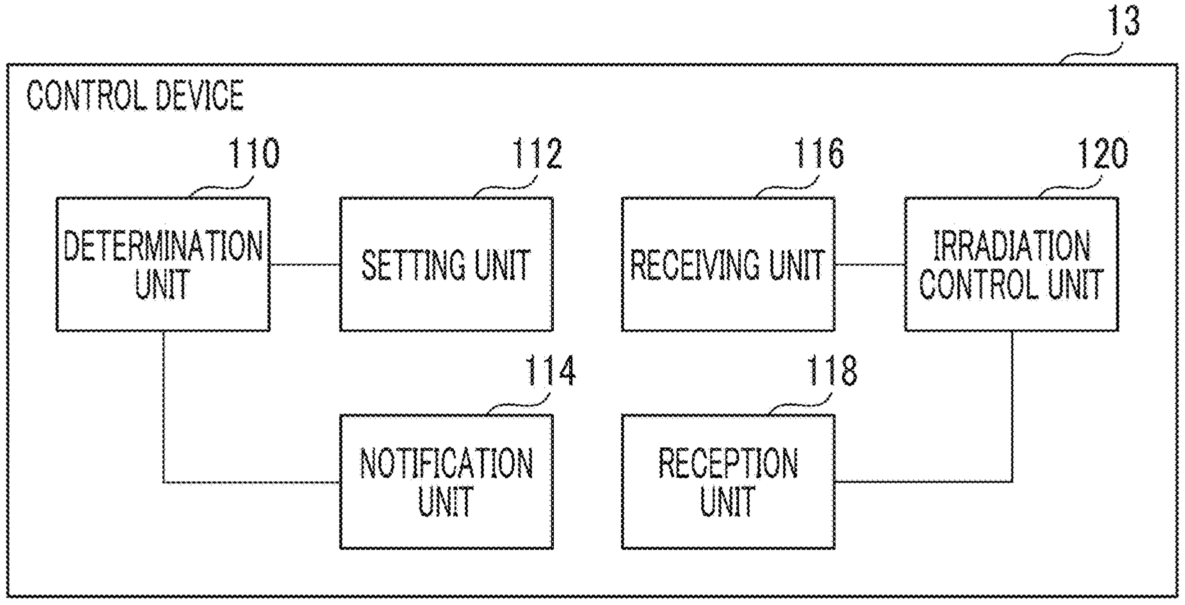
FIG. 5 is a block diagram showing an example of a functional configuration of a control device that controls a radiation source.

Next, a functional configuration of the control device 13 will be described with reference to FIG. 5. As shown in FIG. 5, the control device 13 includes a determination unit 110, a setting unit 112, a notification unit 114, a receiving unit 116, a reception unit 118, and an irradiation control unit 120. The CPU 50 executes the control program 53 to function as the determination unit 110, the setting unit 112, the notification unit 114, the receiving unit 116, the reception unit 118, and the irradiation control unit 120.

The determination unit 110 determines whether or not a condition that an irradiation area of the radiation R on the detection surface of the radiation detector 11 is equal to or less than the maximum area capable of detecting the radiation R in the radiation detector 11 is satisfied. The irradiation area with the radiation R is determined according to the SID and an area of the irradiation opening of the irradiation field limiter 21. In the present embodiment, the determination unit 110 determines whether or not the condition is satisfied by determining whether or not the SID is equal to or less than a first set value and the area of the irradiation opening is equal to or less than a second set value. The first set value and the second set value are determined by standards according to a numerical value (for example, 19 inches) indicating a width of the detection surface of the radiation detector 11 used for fluoroscopy. For example, the determination unit 110 performs the determination in a case where the position of the radiation source 10 is changed or in a case where the positions of the four shielding plates of the irradiation field limiter 21 are changed.

In a case where the positions of the four shielding plates of the irradiation field limiter 21 are fixed, that is, in a case where the area of the irradiation opening is a fixed value, the determination unit 110 may use only the first set value out of the first set value and the second set value. In this case, the determination unit 110 determines whether or not the condition is satisfied by determining whether or not the SID is equal to or less than the first set value. In addition, the determination unit 110 may perform the determination at a predetermined time interval.

In addition, for example, the first set value and the second set value may be designated by the operator. In this case, the CPU 50 receives designation of the first set value and the second set value by the operator.

In a case where the determination unit 110 determines that the condition is satisfied, the setting unit 112 sets an imaging mode to a fluoroscopy mode. In this case, the setting unit 112 transmits an instruction to set the imaging mode to the fluoroscopy mode to the control device 18, and the CPU 90 of the control device 18 sets the imaging mode to the fluoroscopy mode.

In addition, in a case where the determination unit 110 determines that the condition is not satisfied, the setting unit 112 sets the imaging mode to a general imaging mode. In this case, the setting unit 112 transmits an instruction to set the imaging mode to the general imaging mode to the control device 18, and the CPU 90 of the control device 18 sets the imaging mode to the general imaging mode. In the present embodiment, the general imaging mode is set as an initial imaging mode at the time of activation of the system, that is, a default imaging mode.

The processing of setting the imaging mode to any one of the general imaging mode or the fluoroscopy mode is performed, for example, by setting a value indicating the imaging mode stored in a storage unit of each device to a value indicating any one of the general imaging mode or the fluoroscopy mode. The value indicating the imaging mode may be stored in a shared storage unit that is accessible from each apparatus. In addition, the imaging mode may be set by a physical switch.

In a case where the determination unit 110 determines that the condition is satisfied, the notification unit 114 notifies that the condition is satisfied. For example, the notification unit 114 notifies that the condition is satisfied by blinking a display provided in the radiation source 10. The notification unit 114 may notify that the condition is satisfied by a voice output via a speaker. In addition, the notification unit 114 may notify that the condition is satisfied by fixing the radiation source 10 such that the position of the radiation source 10 cannot be changed, such as locking a moving mechanism of the radiation source 10.

In addition, the notification unit 114 may output instruction information indicating an instruction for the notification to the first image processing device 16A. In this case, the CPU 70 of the first image processing device 16A may notify that the condition is satisfied by performing control of displaying a message indicating that the condition is satisfied on the display 17. In addition, the notification unit 114 may output instruction information indicating an instruction for the notification to the console 14. In this case, the CPU 60 of the console 14 may notify that the condition is satisfied by performing control of displaying a message indicating that the condition is satisfied on the display 65.

The receiving unit 116 receives the irradiation condition in the general imaging and the irradiation conditions in the fluoroscopy transmitted from the console 14. The reception unit 118 receives a start instruction for the radiography via the irradiation switch.

The irradiation control unit 120 controls the operation of the radiation source 10. Specifically, in a case where the start instruction for the radiography is received by the reception unit 118 and the imaging mode is the general imaging mode, the irradiation control unit 120 operates the voltage generator 12 according to the irradiation condition in the general imaging received by the receiving unit 116 and causes the radiation tube 20 to emit the radiation R. In addition, in a case where the start instruction for the radiography is received by the reception unit 118 and the imaging mode is the fluoroscopy mode, the irradiation control unit 120 operates the voltage generator 12 according to the irradiation condition in the fluoroscopy received by the receiving unit 116 and causes the radiation tube 20 to emit the radiation R.

In addition, the irradiation control unit 120 outputs an irradiation start signal for notifying the start of the irradiation with the radiation R and an irradiation end signal for notifying the end of the irradiation with the radiation R to the control device 18.

Figure 6:
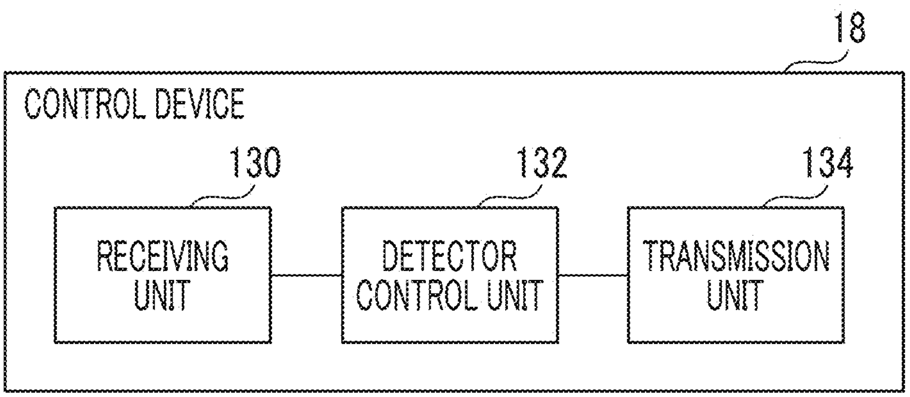
FIG. 6 is a block diagram showing an example of a functional configuration of a control device that controls the radiation detector.

Next, a functional configuration of the control device 18 will be described with reference to FIG. 6. As shown in FIG. 6, the control device 18 includes a receiving unit 130, a detector control unit 132, and a transmission unit 134. The CPU 90 executes the control program 93 to function as the receiving unit 130, the detector control unit 132, and the transmission unit 134.

The receiving unit 130 receives an irradiation start signal and an irradiation end signal transmitted from the control device 13. The detector control unit 132 controls an operation of the radiation detector 11. Specifically, in a case where the imaging mode is the fluoroscopy mode, the detector control unit 132 causes the radiation detector 11 to start processing of continuously acquiring the image at a predetermined frame rate regardless of whether or not an instruction to start the irradiation with the radiation R is received.

That is, in a case where the imaging mode of the radiation detector 11 is set to the fluoroscopy mode, the detector control unit 132 causes the radiation detector 11 to start processing of continuously acquiring the image by causing the detection panel 41 to repeatedly perform a charge accumulation operation and a charge readout operation according to the frame rate. Therefore, in a case where the imaging mode is the fluoroscopy mode, the acquisition of the image is started even before the start of the irradiation with the radiation R. The acquired image can be used as an offset correction image. In addition, since the acquisition of the image is started even before the start of the irradiation with the radiation R, a saturation of temperature rise of the detection panel 41 can be promoted.

In addition, in a case where the imaging mode is the general imaging mode, and the irradiation start signal is received by the receiving unit 130, the detector control unit 132 causes the detection panel 41 to perform the charge accumulation operation. In addition, in a case where the imaging mode is the general imaging mode, and the irradiation end signal is received by the receiving unit 130, the detector control unit 132 causes the detection panel 41 to perform the charge readout operation. As a result, in the general imaging mode, one radiation image is acquired.

In a case where the imaging mode is the general imaging mode, the transmission unit 134 transmits the first radiation image obtained by the control of the detector control unit 132 to the first image processing device 16A. In addition, in a case where the imaging mode is the fluoroscopy mode, the transmission unit 134 sequentially transmits the second radiation images obtained at a predetermined frame rate by the control of the detector control unit 132 to the second image processing device 16B.

Figure 7:
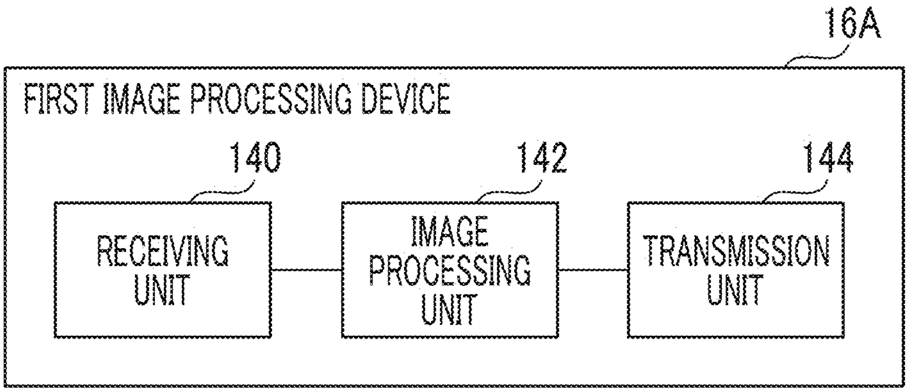
FIG. 7 is a block diagram showing an example of a functional configuration of a first image processing device.

Next, a functional configuration of the first image processing device 16A will be described with reference to FIG. 7. As shown in FIG. 7, the first image processing device 16A includes a receiving unit 140, an image processing unit 142, and a transmission unit 144. The CPU 70 executes the image processing program 73 to function as the receiving unit 140, the image processing unit 142, and the transmission unit 144.

The receiving unit 140 receives the first radiation image transmitted from the radiation detector 11. The image processing unit 142 performs various types of image processing, such as offset correction processing, sensitivity correction processing, and defective pixel correction processing, on the first radiation image received by the receiving unit 140.

The offset correction processing is processing of subtracting, from the radiation image, an offset correction image acquired in a state in which there is no irradiation with the radiation R, in units of pixels. The sensitivity correction processing is processing of correcting variation in sensitivity of each pixel of the detection panel 41 of the radiation detector 11, variation in output characteristic of a circuit that reads out the signal charge, and the like based on sensitivity correction data. The defective pixel correction processing is processing of linearly interpolating a pixel value of a defective pixel with a pixel value of a surrounding normal pixel based on information on a defective pixel having an abnormal pixel value generated during shipment, periodic inspection, or the like.

The transmission unit 144 transmits the first radiation image that has undergone the image processing by the image processing unit 142 to the console 14.

Figure 8:
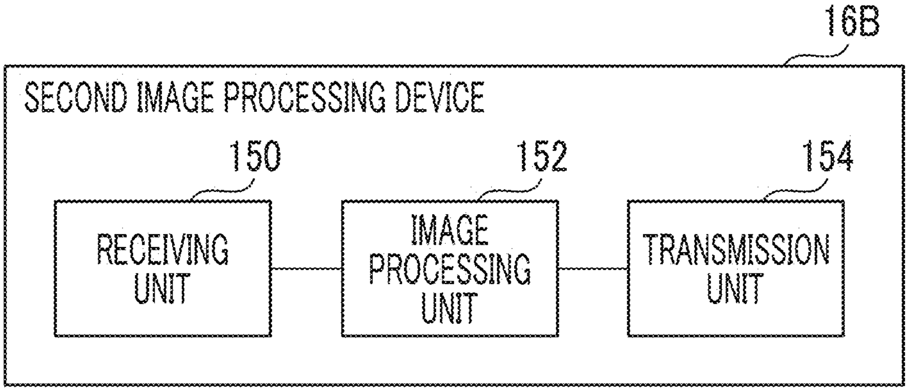
FIG. 8 is a block diagram showing an example of a functional configuration of a second image processing device.

Next, a functional configuration of the second image processing device 16B will be described with reference to FIG. 8. As shown in FIG. 8, the second image processing device 16B includes a receiving unit 150, an image processing unit 152, and a transmission unit 154. The FPGA 80 executes logic programmed in advance to function as the receiving unit 150, the image processing unit 152, and the transmission unit 154.

The receiving unit 150 receives the second radiation image transmitted from the radiation detector 11. The image processing unit 152 performs various types of image processing, such as offset correction processing, sensitivity correction processing, and defective pixel correction processing, on the second radiation image received by the receiving unit 150. The transmission unit 154 transmits the second radiation image that has undergone the image processing by the image processing unit 152 to the console 14.

As described above, the CPU 70 that is a first processor that performs the image processing on the first radiation image obtained in a case where the imaging mode is the general imaging mode, and the FPGA 80 that is a second processor that performs the image processing on the second radiation image obtained in a case where the imaging mode is the fluoroscopy mode are different processors. Since the image processing is performed on the second radiation image at a high speed by the FPGA 80 that is a processor dedicated to fluoroscopy, in which logic is programmed in advance, a high frame rate can be realized.

Figure 9:
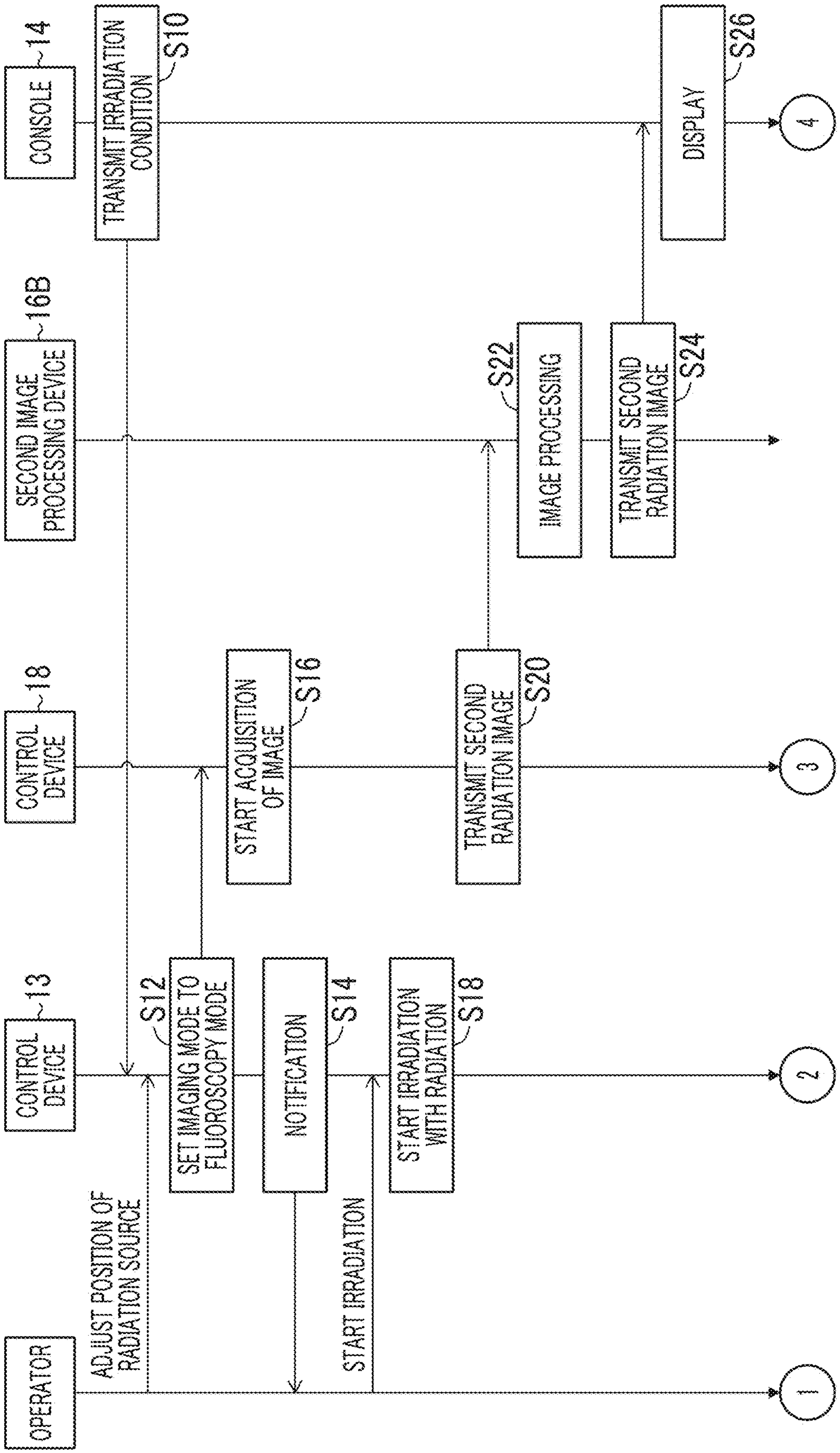
FIG. 9 is a sequence diagram showing an example of radiography processing.
Figure 10:
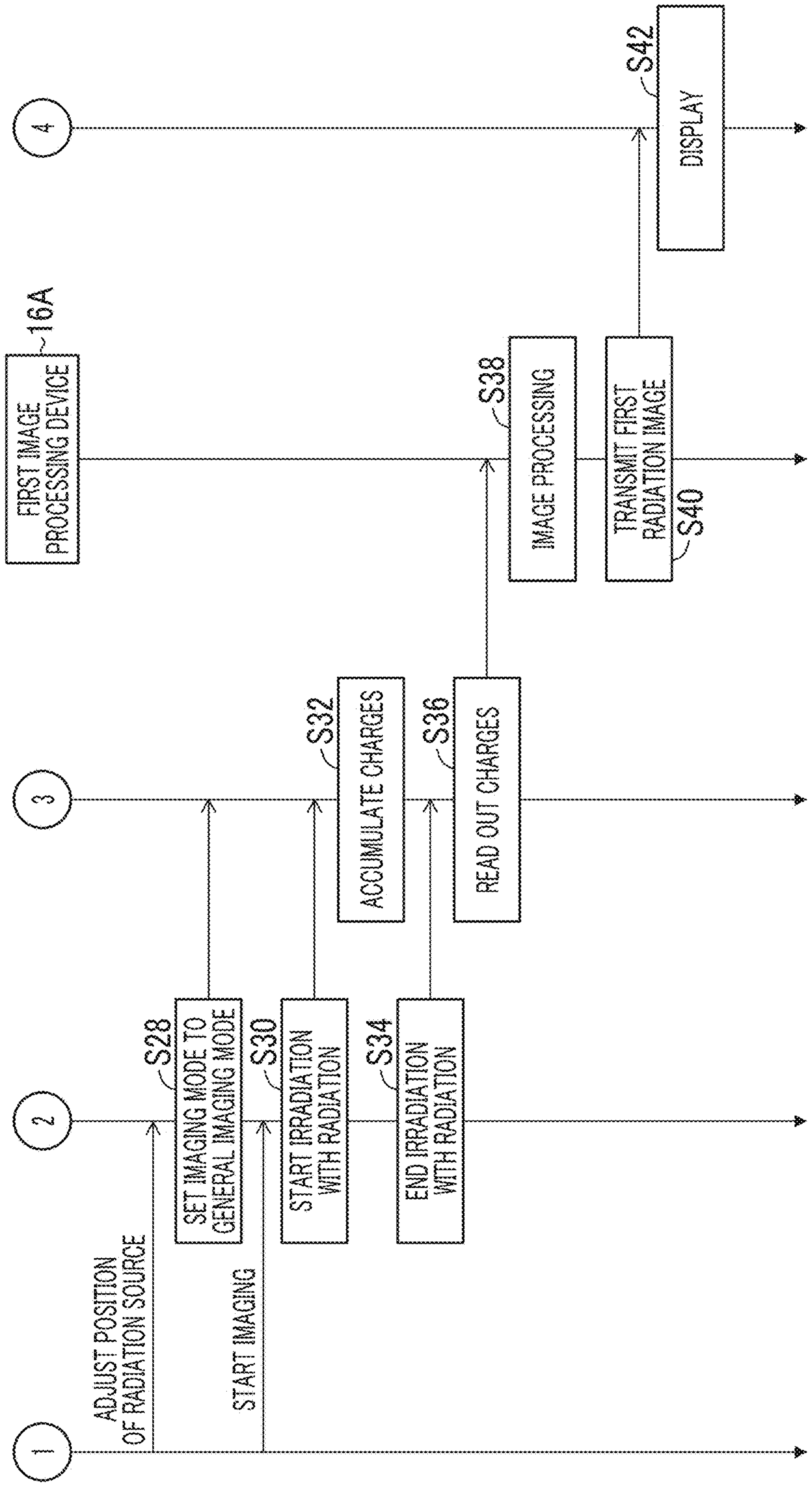
FIG. 10 is a sequence diagram showing an example of the radiography processing.

Next, an operation of the radiography system 2 will be described with reference to FIGS. 9 and 10. FIGS. 9 and 10 are sequence diagrams showing an example of radiography processing executed by the radiography system 2. Here, as an example, a flow of processing in a case where the general imaging is performed after the fluoroscopy will be described.

In a case where the imaging order 66 is registered, in step S10, the acquisition unit 100 acquires the imaging order 66 from the storage unit 62. Then, the transmission unit 102 transmits the irradiation condition in the general imaging and the irradiation condition in the fluoroscopy imaging according to the imaging order 66 acquired by the acquisition unit 100, to the control device 13. The receiving unit 116 receives the irradiation condition in the general imaging and the irradiation condition in the fluoroscopy transmitted from the console 14 in step S10.

The operator makes the patient P stand in front of the upright imaging stand 15S or makes the patient P lie on the top plate 32 of the decubitus imaging table 15L according to the imaging order 66. Then, the operator adjusts the position of the radiation source 10. According to the adjustment of the position of the radiation source 10 by the operator, the determination unit 110 determines whether or not a condition that the irradiation area of the radiation R on the detection surface of the radiation detector 11 is equal to or less than the maximum area capable of detecting the radiation R in the radiation detector 11 is satisfied. In a case where the determination unit 110 determines that the condition is satisfied, in step S12, the setting unit 112 sets the imaging mode to the fluoroscopy mode as described above. Next, in step S14, the notification unit 114 notifies that the condition is satisfied as described above.

In a case where the imaging mode is set to the fluoroscopy mode, in step S16, the detector control unit 132 causes the radiation detector 11 to start processing of continuously acquiring images at a predetermined frame rate, as described above.

The operator receives the notification in step S14 and inputs the start instruction for the radiography via the irradiation switch. The reception unit 118 receives a start instruction for the radiography via the irradiation switch. In a case where the start instruction is received by the reception unit 118, in step S18, the irradiation control unit 120 operates the voltage generator 12 according to the irradiation condition in the fluoroscopy received by the receiving unit 116 to emit the radiation R from the radiation tube 20. As a result, the irradiation with the radiation R is started.

In step S20, the transmission unit 134 sequentially transmits the second radiation image obtained at a predetermined frame rate by the control of the detector control unit 132 to the second image processing device 16B. The receiving unit 150 receives the second radiation image transmitted from the radiation detector 11 in step S20.

In step S22, as described above, the image processing unit 152 performs various types of image processing on the second radiation image received by the receiving unit 150. In step S24, the transmission unit 154 transmits the second radiation image that has undergone the image processing in step S22 to the console 14. The receiving unit 104 receives the second radiation image transmitted from the second image processing device 16B in step S24. In step S26, the display control unit 106 performs control to display a plurality of the second radiation images continuously received by the receiving unit 104 on the display 65 according to a frame rate.

The operator ends the fluoroscopy by ending the irradiation with the radiation R. In addition, in a case where the fluoroscopy ends, the operator adjusts the position of the radiation source 10 in accordance with the general imaging. According to the adjustment of the position of the radiation source 10 by the operator, the determination unit 110 determines whether or not a condition that the irradiation area of the radiation R on the detection surface of the radiation detector 11 is equal to or less than the maximum area capable of detecting the radiation R in the radiation detector 11 is satisfied. In a case where the determination unit 110 determines that the condition is not satisfied, in step S28, the setting unit 112 sets the imaging mode to the general imaging mode as described above.

Next, the operator inputs the start instruction for the radiography via the irradiation switch. The reception unit 118 receives a start instruction for the radiography via the irradiation switch. In a case where the start instruction is received by the reception unit 118, in step S30, the irradiation control unit 120 operates the voltage generator 12 according to the irradiation condition in the general imaging received by the receiving unit 116 to emit the radiation R from the radiation tube 20. As a result, the irradiation with the radiation R is started. Then, the irradiation control unit 120 outputs an irradiation start signal for notifying the start of the irradiation with the radiation R to the control device 18. The receiving unit 130 receives the irradiation start signal transmitted from the control device 13 in step S30.

In a case where the irradiation start signal is received by the receiving unit 130, in step S32, the detector control unit 132 causes the detection panel 41 to perform the charge accumulation operation. In a case where the irradiation time of the radiation R started in step S30 has elapsed, in step S34, the irradiation control unit 120 ends the irradiation with the radiation R from the radiation tube 20. Then, the irradiation control unit 120 outputs an irradiation end signal for notifying the end of the irradiation with the radiation R to the control device 18. The receiving unit 130 receives the irradiation end signal transmitted from the control device 13 in step S34.

In a case where the irradiation end signal is received by the receiving unit 130, in step S36, the detector control unit 132 causes the detection panel 41 to perform the charge readout operation. Then, the transmission unit 134 transmits the first radiation image obtained by the readout operation to the first image processing device 16A. The receiving unit 140 receives the first radiation image transmitted from the radiation detector 11 in step S36.

In step S38, as described above, the image processing unit 142 performs various types of image processing on the first radiation image received by the receiving unit 140. In step S40, the transmission unit 144 transmits the first radiation image that has undergone the image processing in step S38 to the console 14. The receiving unit 104 receives the first radiation image transmitted from the first image processing device 16A in step S40. In step S42, the display control unit 106 performs control to display the first radiation image received by the receiving unit 104 on the display 65.

As described above, according to the present embodiment, in the radiography system that can execute the fluoroscopy and the general imaging in a switchable manner, the imaging efficiency can be improved.

In the above-described embodiment, in the fluoroscopy mode, the operator may be able to input an instruction to capture a still image. In this case, in a case where the imaging mode is the fluoroscopy mode and the instruction to capture the still image is received, the CPU 60 of the console 14 may generate a single radiation still image using one or more radiation images obtained by the fluoroscopy. For example, the CPU 60 may generate one radiation still image by generating an average image of a plurality of the radiation images obtained by the fluoroscopy. In addition, generation processing of the radiation still image may be executed by a processor of a device other than the console 14, such as the FPGA 80 of the second image processing device 16B.

In addition, each functional unit in the above-described embodiment may be provided in a device different from a device in which the functional units are provided in the above-described embodiment. In addition, each functional unit in the above-described embodiment may be realized by one computer.

In addition, in the above-described embodiment, for example, various processors shown below can be used as a hardware structure of a processing unit that executes various types of processing, such as each functional unit of each device. The various processors include, in addition to a CPU that is a general-purpose processor functioning as various processing units by executing software (program) as described above, a programmable logic device (PLD) that is a processor whose circuit configuration can be changed after manufacture such as an FPGA, a dedicated electric circuit that is a processor having a circuit configuration dedicatedly designed to execute specific processing such as an application specific integrated circuit (ASIC), and the like.

One processing unit may be configured by one of the various processors, or may be configured by a combination of the same type or different types of two or more processors (for example, a combination of a plurality of FPGAs or a combination of the CPU and the FPGA). A plurality of processing units may be configured by one processor.

As an example of configuring a plurality of processing units with one processor, first, there is a form in which, as represented by computers such as a client and a server, one processor is configured by combining one or more CPUs and software, and the processor functions as a plurality of processing units. Second, as represented by a system on chip (SoC) or the like, there is a form in which a processor that realizes functions of an entire system including a plurality of processing units with one integrated circuit (IC) chip is used. As described above, the various processing units are configured using one or more of the various processors as a hardware structure.

Furthermore, as the hardware structure of the various processors, more specifically, an electric circuitry in which circuit elements such as semiconductor elements are combined can be used.

In the above-described embodiment, an aspect in which various programs are stored (installed) in the storage unit in advance has been described, but the present disclosure is not limited thereto. The various programs may be provided in a form of being recorded on a recording medium such as a compact disc read only memory (CD-ROM), a digital versatile disc read only memory (DVD-ROM), and a Universal Serial Bus (USB) memory. The various programs may be provided in a form of being downloaded from an external device via a network.

What is claimed is:

1. A radiography system capable of executing fluoroscopy in which a plurality of radiation images are continuously captured at a predetermined frame rate and general imaging in which one radiation image is recorded in a switchable manner, the radiography system comprising at least one processor, wherein the processor is configured to:

set an imaging mode to a fluoroscopy mode in a case where a condition that an irradiation area of radiation on a detection surface of a radiation detector is equal to or less than a maximum area capable of detecting the radiation in the radiation detector is satisfied; and cause the radiation detector to start processing of continuously acquiring images at the predetermined frame rate by repeatedly performing a charge accumulation operation and a charge readout operation before irradiation with the radiation is started, regardless of whether or not an instruction to start irradiation with the radiation is received in a case where the imaging mode is the fluoroscopy mode.

2. The radiography system according to claim 1, wherein the processor is configured to, in a case where the condition that the irradiation area is equal to or less than the maximum area is satisfied, notify that the condition is satisfied.

3. The radiography system according to claim 1, wherein the processor is configured to set the imaging mode to a general imaging mode in a case where the condition that the irradiation area is equal to or less than the maximum area is not satisfied.

4. The radiography system according to claim 2, wherein the processor is configured to set the imaging mode to a general imaging mode in a case where the condition that the irradiation area is equal to or less than the maximum area is not satisfied.

5. The radiography system according to claim 1, wherein the condition is a condition that a distance from a radiation source to the detection surface is equal to or less than a set value.

6. The radiography system according to claim 2, wherein the condition is a condition that a distance from a radiation source to the detection surface is equal to or less than a set value.

7. The radiography system according to claim 1, wherein a plurality of processors are provided, and a first processor that performs image processing on the radiation image obtained in a case where the imaging mode is a general imaging mode and a second processor that performs image processing on the radiation image obtained in a case where the imaging mode is the fluoroscopy mode are different processors.

8. The radiography system according to claim 2, wherein a plurality of processors are provided, and a first processor that performs image processing on the radiation image obtained in a case where the imaging mode is a general imaging mode and a second processor that performs image processing on the radiation image obtained in a case where the imaging mode is the fluoroscopy mode are different processors.

9. The radiography system according to claim 7, wherein the second processor includes a logic circuit in which logic of image processing performed on the radiation image is programmed in advance.

10. The radiography system according to claim 8, wherein the second processor includes a logic circuit in which logic of image processing performed on the radiation image is programmed in advance.

11. The radiography system according to claim 1, wherein the processor is configured to, in a case where the imaging mode is the fluoroscopy mode, and an instruction to capture a still image is received, generate a single radiation still image using one or more radiation images obtained by the fluoroscopy.

12. The radiography system according to claim 2, wherein the processor is configured to, in a case where the imaging mode is the fluoroscopy mode, and an instruction to capture a still image is received, generate a single radiation still image using one or more radiation images obtained by the fluoroscopy.

13. The radiography system according to claim 5, wherein the processor is configured to receive designation of the set value.

14. The radiography system according to claim 6, wherein the processor is configured to receive designation of the set value.

15. The radiography system according to claim 1, wherein the processor is configured to use at least one image acquired before the irradiation with the radiation is started as an offset correction image.

16. The radiography system according to claim 1, wherein, in a case where the imaging mode is a general imaging mode, the radiation detector performs the charge accumulation operation in response to an irradiation start signal and performs the charge readout operation after a predetermined time has passed.

17. The radiography system according to claim 1, wherein the processor is configured to determine whether the condition is satisfied based on a distance from a radiation source to the detection surface and an area of an irradiation opening of an irradiation field limiter.

18. A radiography method for a radiography system including at least one processor and capable of executing fluoroscopy in which a plurality of radiation images are continuously captured at a predetermined frame rate and general imaging in which one radiation image is recorded in a switchable manner, the radiography method comprising:

causing the processor to execute processing of setting an imaging mode to a fluoroscopy mode in a case where a condition that an irradiation area of radiation on a detection surface of a radiation detector is equal to or less than a maximum area capable of detecting the radiation in the radiation detector is satisfied, and causing the radiation detector to start processing of continuously acquiring an image at the predetermined frame rate by repeatedly performing a charge accumulation operation and a charge readout operation before irradiation with the radiation is started, regardless of whether or not an instruction to start irradiation with the radiation is received in a case where the imaging mode is the fluoroscopy mode.

19. A non-transitory computer-readable storage medium storing a radiography program for a radiography system including at least one processor and capable of executing fluoroscopy in which a plurality of radiation images are continuously captured at a predetermined frame rate and general imaging in which one radiation image is recorded in a switchable manner, the radiography program causing the processor to execute processing of:

setting an imaging mode to a fluoroscopy mode in a case where a condition that an irradiation area of radiation on a detection surface of a radiation detector is equal to or less than a maximum area capable of detecting the radiation in the radiation detector is satisfied; and causing the radiation detector to start processing of continuously acquiring an image at the predetermined frame rate by repeatedly performing a charge accumulation operation and a charge readout operation before irradiation with the radiation is started, regardless of whether or not an instruction to start irradiation with the radiation is received in a case where the imaging mode is the fluoroscopy mode.

* * * * *